US005240005A

United States Patent [19]

Viebach

[11] Patent Number: 5,240,005

[45] Date of Patent: Aug. 31, 1993

[54] ACOUSTIC FOCUSSING DEVICE

[75] Inventor: Thomas Viebach, Pischertshofen, Fed. Rep. of Germany

[73] Assignee: Dornier Medizintechnik GmbH, Fed. Rep. of Germany

[21] Appl. No.: 796,341

[22] Filed: Nov. 22, 1991

[30] Foreign Application Priority Data

Nov. 22, 1990 [DE] Fed. Rep. of Germany ....... 4037160

[51] Int. Cl.[5] ......................... A61B 8/00; A61B 17/22

[52] U.S. Cl. ........................... 128/663.01; 128/24 EL

[58] Field of Search ......... 128/24 EL, 660.03, 662.01; 606/127-128

[56] References Cited

U.S. PATENT DOCUMENTS 4,630,607 12/1986 Duinker et al. ................ 128/24 EL
4,674,505 6/1987 Pauli et al. ..................... 128/24 EL
4,718,421 1/1988 Rohwedder et al. .......... 128/660.03
4,823,773 4/1989 Naser et al. .................... 128/24 EL
4,840,166 6/1989 Naser et al. .................... 128/24 EL

FOREIGN PATENT DOCUMENTS 3328051 2/1985 Fed. Rep. of Germany .
8523024 3/1987 Fed. Rep. of Germany .
3605277 8/1987 Fed. Rep. of Germany .
3735993 5/1989 Fed. Rep. of Germany ... 128/24 EL
3739393 6/1989 Fed. Rep. of Germany .

*Primary Examiner*—Francis Jaworski
*Attorney, Agent, or Firm*—Evenson, McKeown, Edwards & Lenahan

[57] ABSTRACT

The present invention relates to an acoustic focussing device for the focussing of ultrasonic and shock waves, particularly for the no-contact crushing of a concrement disposed in the body of a living being. Several boundary surfaces are arranged behind one another in the propagating direction of the sound waves, in which case adjacent gaps contain liquids of different sound velocities. At least one gap is connected with a non-adjacent gap. At least one of the boundary surfaces is deformable. At least one of the boundary surfaces can be moved in parallel to the propagating direction of the sound waves by means of which movement liquid is displaced between connected gaps and the radius of curvature of at least one of the deformable boundary surfaces is changed.

18 Claims, 2 Drawing Sheets

ACOUSTIC FOCUSSING DEVICE

BACKGROUND AND SUMMARY OF THE INVENTION

This invention relates to an acoustic focussing device, particularly for the focussing of ultrasonic and shock waves for the no-contact crushing of a concrement disposed in the body of a living being.

For the focussing of flat or slightly curved shock wave fronts, as they are generated in the case of lithotrity instruments which operate, for example, according to the electromagnetic or piezoelectric converter principle, an acoustic lens system is required. In body, the focussed shock wave is aligned with the stone to be treated. In this case, depending on the position of the stone, different penetration depths of the shock wave are required.

The requirement of the variable penetration depth can be met by systems with a fixed focal length and with an additional variable forward-flow path (such as a bellows-shaped water cushion) or by a system with a variable focal length.

Other requirements with respect to a therapy unit for lithotrity are, for example, the overall size, the weight as well as technical expenditures that should be as low as possible in the case of the peripheral equipment (such as a position-independent, sensitive pressure/volume control).

In the German Patent Document DE 85 23 024 U1, an ultrasonic generator is indicated which has a deformable boundary surface between the coupling surface to the patient's body and a piezoelectric converter, the curvature of this boundary surface being changeable by the change of the pressure in the adjacent liquid. As an alternative, the focus displacement may also be achieved by the shifting of an additional solid-state lens.

In the German Patent Document DE 37 39 393 A1, a lithotritor is described with an adjustable focussing in which the wall of a liquid immersion objective is connected with a part of an adjusting device. By moving the adjusting device in the shock wave propagation direction, the curvature of the wall will change.

In the German Patent Document DE 33 28 051 A1, a device is described for the no-contact crushing of concrements in which the change of the focal point is achieved by the shifting of one or several acoustic lenses.

From the German Patent Document DE 36 05 277 A1, a shock wave therapy device is known in which a lens is surrounded by the coupling medium, in which case the liquid areas in front of and behind the lens are connected with one another.

It is an object of the present invention to provide a focussing device of a very small overall size whose focal length (focal intercept) can be varied within a wide range and, in addition, reduces the technical expenditures in the case of therapy instruments. In this case and in the following, the focal length F or the focal intercept of a lens system is the distance between the focus and the closest point of the—viewed from the direction of the shock wave source—last refractive surface of the lens system.

The object is achieved according to preferred embodiments of the invention by providing a system comprising:

a housing, a plurality of boundary surfaces in the housing which define gap spaces arranged behind one another in a sound propagating direction of sound waves to be focussed, a first fluid disposed in one of said gap spaces, a second fluid disposed in another of said gap spaces which is separated from the first gap space by one of the boundary surfaces, said one boundary surface being flexibly deformable, said first and second fluids exhibiting different sound transmission velocity characteristics, and a boundary shifting device for shifting at least one of the boundary surfaces in parallel to a sound propogating direction of sound waves to be focussed such that at least one of said fluids is displaced between two of the gap spaces with consequent deformation of the one flexibly deformable boundary surface to change the radius of curvature thereof and thus change the focus of said focussing device.

According to the invention, several boundary surfaces are arranged behind one another in the propagation direction of the sound waves, in which case adjacent gaps contain liquids of different sound velocities. In this case, these boundary surfaces may consist of material s which are nondeformable; that is, their form is particularly not affected by pressure differences between liquids bordering on both sides of the boundary surface. However, at least one of the boundary surfaces is made of a deformable material; that is, a deforming of this boundary surface as a result of pressure differences between the bordering liquids is possible. At least one of the boundary surfaces may be displaced in parallel to the propagation direction of the sound waves and may then be locked in its position. At least one gap is connected with a non-adjacent gap.

By means of the shifting of the movable boundary surfaces, the liquid is displaced between the connected gaps, and as a result the radius of curvature of at least one of the deformable boundary surfaces is changed.

A change of the refractive characteristics of the whole focussing device, particularly the refractive power and the local length F, therefore finally results in two effects:

1. Change of position of one or several shifted boundary surfaces;
2. Change of refractive power of one or several deformable boundary surfaces because of their deformation.

Other objects, advantages and novel features of the present invention will become apparent from the following detailed description of the invention when considered in conjunction with the accompanying drawings.

DETAILED DESCRIPTION OF THE DRAWINGS

Figure 1A:
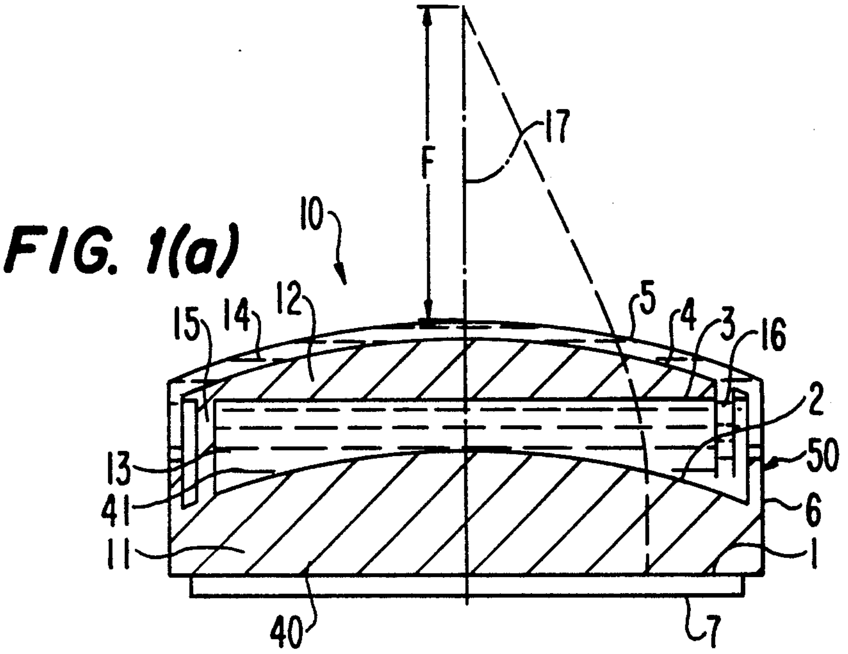
FIG. 1*a* is a cross-sectional schematic view of a development of a focussing device constructed according to a preferred embodiment of the invention, shown in a first focal length position.

FIG. 1a is a cross-sectional view of a focussing device 10 according to the invention. The base area 1 of a cylindrical tube 6, which is closed off by the coupling surface 5 to the patient's body, forms a sound source 7, for example, a shock wave source according to the electromagnetic or piezomagnetic converter principle. By means of component 50, which in the following will be called a lens group and which comprises the boundary surfaces 2, 3, 4, the volume inside the tube 6 is divided into two volume areas which are filled with two liquids 40, 41 of different sound velocities. These two volume areas, in turn, are divided into gaps 11, 12 and 13, 14, gaps 11, 12 being connected with one another by access 15, and gaps 13, 14 being connected with one another by access 16. Thus, the first liquid 40 is situated in gaps 11, 12, and the second liquid 41 is situated in gaps 13, 14. A wave front generated in the sound source 7 travels successively through the liquids in the gaps 11, 13, 12, 14 until it is led to the patient's body by way of the coupling surface 5. In this case, transition take place at the boundary surfaces 2, 3, 4 between the two liquids 40, 41 of different sound velocities.

The lens group 50 can be displaced inside the tube 6 in parallel to its walls. By means of sliding packings at the contact points of the lens group 50 and the tube wall, also during the displacement, the exchange between the two liquids 40, 41 is prevented in the gaps 11, 12, and 13, 14.

Surfaces 2, 4 of the lens group 50 are nondeformable, while surface 3 consists of an elastic material and is therefore deformable.

When the lens group 50 is displaced in the direction of the sound source 7 with consequent movement of the non-deformable boundary surfaces 2 and 4, liquid 40 is pushed out of the gap 11 and flows through the access 15 into gap 12. As a result, the form-flexible boundary surface 3 is arched and displaces liquid 41 from the gap 13 through the access 16 into the gap 14. The amounts of substance of each of the two liquids 40, 41 in the gaps 11, 12 and 13, 14 stay the same before, during and after the displacement.

In order to maintain a focussing system in the case of the radii of curvature of the boundary surfaces 2, 3, 4, 5 illustrated here, the liquid 40 in gaps 11, 12 is to be selected such that it has a lower sound velocity than liquid 41 in gaps 13, 14. One example in this case is $H_2O$ in gaps 11, 12 and glycerin in gaps 13, 14.

In an advantageous embodiment, the coupling surface 5 is selected to be nondeformable. Its refractive effect is generally determined from the sound velocity in the adjacent liquid 41 in gap 14 in relationship to that in the patient's body. When the liquid 41 is gap 14 is selected such that these two sound velocities are identical, the coupling surface 5 has no refractive effect.

Under this condition, it is particularly advantageous according to certain preferred embodiments that it be made of deformable materials because this facilitates the coupling to the patient'body.

Figure 1B:
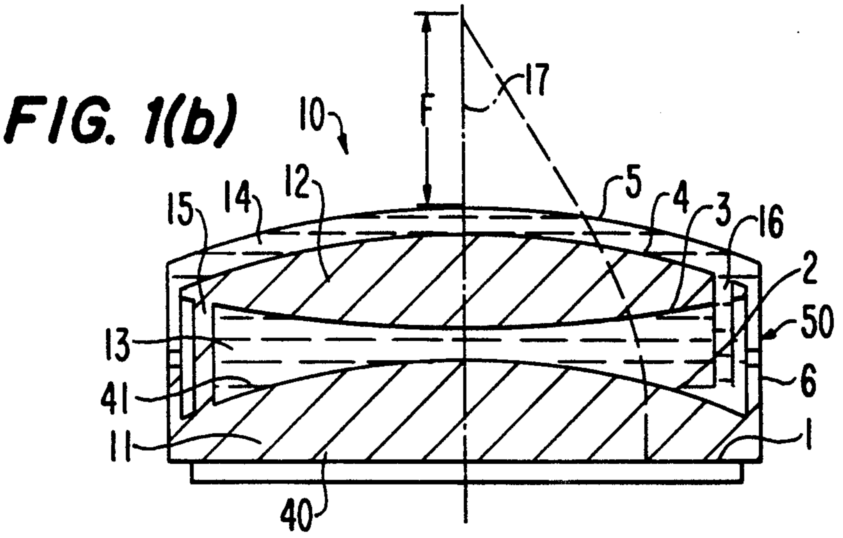
FIG. 1*b* is a view of the device of FIG. 1*a*, shown in a second focal length position.
Figure 1C:
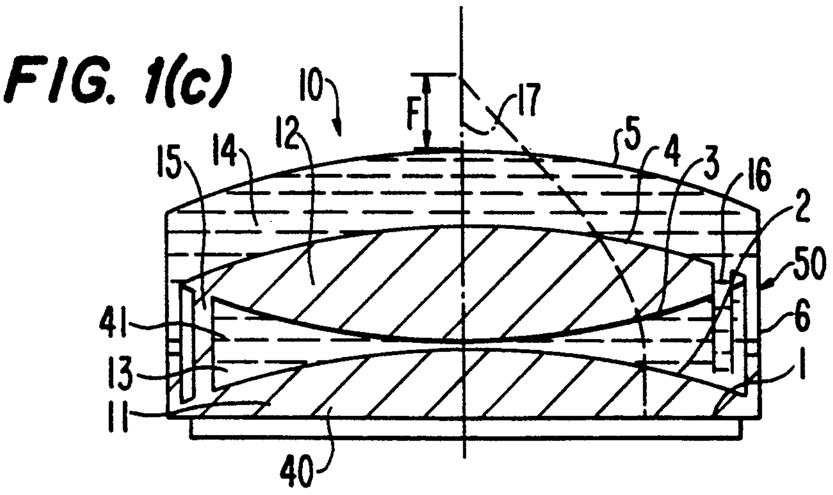
FIG. 1*c* is a view of the device of FIG. 1*a*, shown in a third focal length position.

For the control of the focal length F, only the position of the movable lens group 50 is important. FIGS. 1b and 1c show the same focussing device 10 as FIG. 1a, in which case, however, the movable lens group 50 inside the cylindrical tube 6 is in different positions. This results in a respective different curvature of the deformable boundary surface 3 which, in turn, results in a different refractive power of this boundary surface 3 and thus also of the whole focussing device 10. This refractive power change as well as the change of the position of the boundary surfaces 2, 3, 4 inside the tube 6 contribute to the change of the focal length F.

In addition to the focussing device 10 illustrated here in which boundary surface 3 is constructed to be deformable, embodiments are also contemplated for the achieving of the described advantageous characteristics, with boundary surface 2 or 4 to be deformable.

The following advantages are achieved by means of the invention:

Low overall height: Since the change of the focal length F results from the displacement of the lens group 50 and the focal length change of the flexible boundary surface 3, even a short displacement path will result in a clear focal length change. The overall length of the therapy unit therefore becomes clearly less in comparison to a system with a fixed focal length and a water forward flow path or a system with a fixed-focus shiftable lens.

Pressure and volume control are completely eliminated because the amount of liquid contained in the system remains constant.

Uncomplicated control of the focus position: The focus position is a clear function of the displacement path of the lens group 50. A measuring of the filling degree in the flexible lens (inside the gap 13) is not necessary.

In the case of short focal lengths F, the aperture of the focussing device 10 will increase; that is, the energy density on the skin surface remains low—also in the case of thin patients.

Figure 2A:
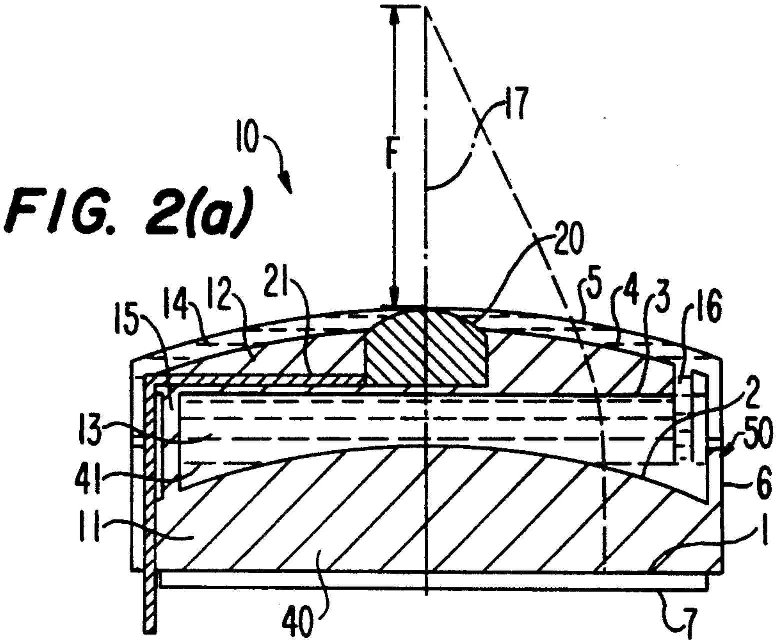
FIG. 2*a* is a cross-sectional schematic view of a development of a focussing device constructed according to another preferred embodiment of the invention with an additional ultrasonic transducer.
Figure 2B:
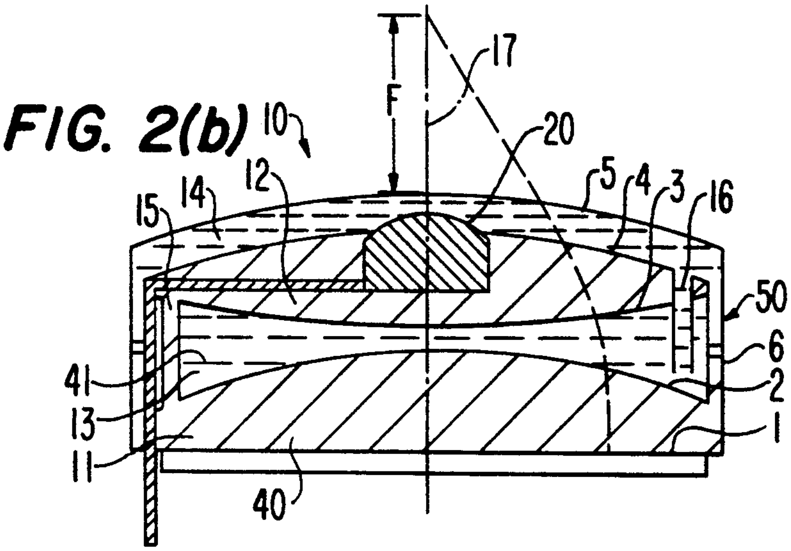
FIG. 2*b* is a view of the device of FIG. 2*a*, shown in a second focal length position.
Figure 2C:
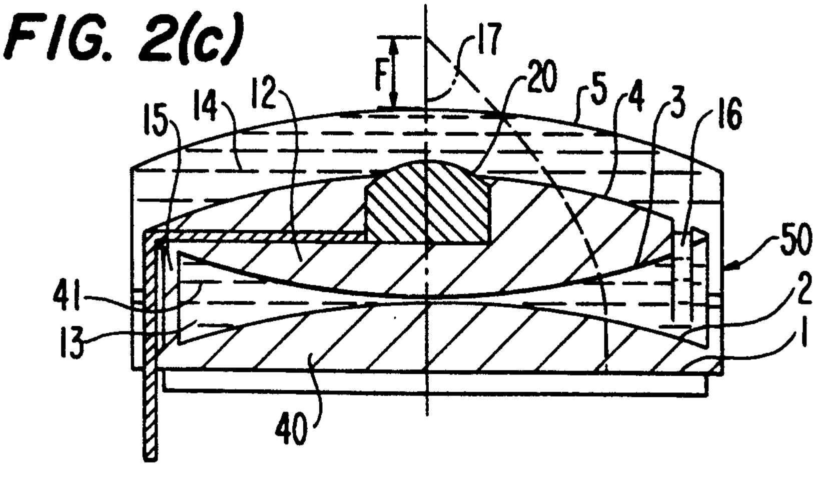
FIG. 2c is a view of the device of FIG. 2a, shown in a third focal length position.

In a particularly advantageous embodiment illustrated in FIGS. 2a, 2b, and 2c, an ultrasonic transducer 20 is integrated into the focussing device 10. FIGS. 2a, 2b, 2c are cross-sectional views of a focussing device 10, in three different adjustment positions of the focal length F which corresponds to that illustrated in FIGS. 1a, 1b, and 1c, but has an additional ultrasonic transducer 20.

The ultrasonic transducer 20 is fastened to the lens group 5 by means of a holding arm 21 so that it is moved along during its displacement. Preferably, the ultrasonic transducer 20 is arranged on the main axis 17 (which in this case corresponds to the tube axis) of the focussing device 10.

By means of the connection with the lens group 50, it is achieved that, in the case of a short focal length F (FIG. 2c), the shadowing of the shock wave by the transducer housing remains minimal, and in the case of large focal lengths F (FIG. 2a), the ultrasonic transducer is situated very closely on the patient's body so that its penetration depth can be optimally utilized.

By means of the displacement of the lens group 50, the focus position relative to the transducer 20 changes less extensively than the focal length F of the focussing device 10; that is, the position of the focus remains in the center image area of the transducer 20 while the imaging quality is good.

Although the invention has been described and illustrated in detail, it is to be clearly understood that the same is by way of illustration and example, and is not to be taken by way of limitation. The spirit and scope of the present invention are to be limited only be the terms of the appended claims.

What is claimed is:

1. An acoustic focussing device for focussing ultrasonic and/or shock waves for medical applications, comprising:

a housing, a plurality of boundary surface means in the housing which define gap spaces, in a sound propagating direction of sound waves to be focussed, a first fluid disposed in one of said gap spaces, a second fluid disposed in another of said gap spaces which is separated from the first gap space by one of the boundary surface means, said one of the boundary surface means being flexibly deformable, and a boundary shifting device means for shifting at least one of the boundary surface means in parallel to a sound propagating direction of sound waves to be focussed such that at least one of said fluids is displaced between two of the gap spaces with consequent deformation of the one flexibly deformable boundary surface means to change the radius of curvature thereof and thus change the focus of said focussing device; and wherein at least one of said gap spaces is fluidly connected with another non-adjacent one of said gap spaces.

2. An acoustic focussing device according to claim 1, wherein said boundary shifting device includes means for moving a plurality of said boundary surface means together.

3. An acoustic focussing device according to claim 1, wherein five of said boundary surface means are provided which define respective first, second, third, and fourth gap spaces as viewed in the propagating direction, wherein said first and third gap spaces are fluidly connected, and wherein said second and fourth gap spaces are fluidly connected.

4. An acoustic focussing device according to claim 3, wherein the second, third, and fourth boundary surface means, viewed in the propagating direction, can be moved independently of one another or jointly.

5. An acoustic focussing device according to claim 3, wherein the second, third, and fourth boundary surface means are arranged on a component which can be moved in parallel to the propagating direction.

6. An acoustic focussing device according to claim 4, wherein the second, third, and fourth boundary surface means are arranged on a component which can be moved in parallel to the propagating direction.

7. An acoustic focussing device according to claim 3, wherein at least one of the second, third, and fourth boundary surface means is deformable.

8. An acoustic focussing device according to claim 6, wherein at least one of the second, third, and fourth boundary surface means is deformable.

9. An acoustic focussing device according to claim 3, wherein the third boundary surface means is deformable.

10. An acoustic focussing device accordign to claim 3, wherein the second boundary surface means is deformable.

11. An acoustic focussing device according to claim 3, wherein the fourth boundary surface means is deformable.

12. An acoustic focussing device according to claim 3, wherein said first and second fluids are liquids.

13. An acoustic focussing device according to claim 12, wherein the substance quantities of all liquids inside the focussing device are constant before, during and after the displacement.

14. An acoustic focussing device according to claim 3, wherein the boundary surface means, which is last viewed in the propagating direction and serves as a coupling surface to the patient's body, is nondeformable.

15. An acoustic focussing device according to claim 3, wherein the boundary surface means, which is last viewed in the propagating direction and serves as a coupling surface to the patient's body, is nondeformable.

16. An acoustic focussing device according to claim 3, wherein an ultrasonic transducer is disposed inside the focussing device housing.

17. An acoustic focussing device according to claim 16, wherein the ultrasonic transducer is situated on the axial main axis of the focussing device and is connected with one of the movable boundary surface means.

18. An acoustic focussing device according to claim 1, wherein said first and second fluids are water and glycerin.

* * * * *